US009795614B2

(12) United States Patent
Grosskreutz et al.

(10) Patent No.: US 9,795,614 B2
(45) Date of Patent: *Oct. 24, 2017

(54) COMPOSITIONS AND METHODS FOR REDUCING BODY FAT

(71) Applicant: Topokine Therapeutics, Inc., Newton, MA (US)

(72) Inventors: Cynthia L. Grosskreutz, Swampscott, MA (US); Louis R. Pasquale, Newton Highlands, MA (US); Michael S. Singer, Newton Center, MA (US); Murat V. Kalayoglu, Silver Spring, MD (US)

(73) Assignee: Topokine Therapeutics, Inc., Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/243,641

(22) Filed: Aug. 22, 2016

(65) Prior Publication Data

US 2016/0354386 A1 Dec. 8, 2016

Related U.S. Application Data

(63) Continuation of application No. 14/838,049, filed on Aug. 27, 2015, now Pat. No. 9,421,215, which is a continuation of application No. 14/504,788, filed on Oct. 2, 2014, now Pat. No. 9,144,574, which is a continuation of application No. 14/180,074, filed on Feb. 13, 2014, now Pat. No. 8,877,807, which is a continuation of application No. 12/652,968, filed on Jan. 6, 2010, now Pat. No. 8,829,050, which is a continuation of application No. 11/712,839, filed on Mar. 1, 2007, now Pat. No. 7,666,912.

(60) Provisional application No. 60/844,337, filed on Sep. 13, 2006, provisional application No. 60/785,360, filed on Mar. 23, 2006.

(51) Int. Cl.
*A61K 31/5575* (2006.01)
*A61K 9/00* (2006.01)
*A61K 8/37* (2006.01)
*A61K 8/42* (2006.01)
*A61Q 19/06* (2006.01)
*A61K 8/69* (2006.01)

(52) U.S. Cl.
CPC .......... *A61K 31/5575* (2013.01); *A61K 8/37* (2013.01); *A61K 8/42* (2013.01); *A61K 8/69* (2013.01); *A61K 9/0014* (2013.01); *A61K 9/0019* (2013.01); *A61K 9/0021* (2013.01); *A61K 9/0024* (2013.01); *A61Q 19/06* (2013.01); *A61K 9/0048* (2013.01)

(58) Field of Classification Search
CPC ................................................. A61K 31/5575
See application file for complete search history.

(56) References Cited

U.S. PATENT DOCUMENTS

| | | | |
|---|---|---|---|
| 4,270,537 A | 6/1981 | Romaine | |
| 4,596,556 A | 6/1986 | Morrow et al. | |
| 4,599,353 A | 7/1986 | Bito | |
| 4,790,824 A | 12/1988 | Morrow et al. | |
| 4,886,499 A | 12/1989 | Cirelli et al. | |
| 4,940,460 A | 7/1990 | Casey et al. | |
| 4,941,880 A | 7/1990 | Burns | |
| 5,011,062 A | 4/1991 | Nakanishi et al. | |
| 5,015,235 A | 5/1991 | Crossman | |
| 5,064,413 A | 11/1991 | McKinnon et al. | |
| 5,141,496 A | 8/1992 | Dalto et al. | |
| 5,190,521 A | 3/1993 | Hubbard et al. | |
| 5,296,504 A | 3/1994 | Stjernschantz et al. | |
| 5,312,335 A | 5/1994 | McKinnon et al. | |
| 5,328,483 A | 7/1994 | Jacoby | |
| 5,334,144 A | 8/1994 | Alchas et al. | |
| 5,339,163 A | 8/1994 | Homma et al. | |
| 5,383,851 A | 1/1995 | McKinnon, Jr. et al. | |
| 5,417,662 A | 5/1995 | Hjertman et al. | |
| 5,422,368 A | 6/1995 | Stjernschantz et al. | |
| 5,466,220 A | 11/1995 | Brenneman | |
| 5,480,381 A | 1/1996 | Weston | |
| 5,503,627 A | 4/1996 | McKinnon et al. | |
| 5,520,639 A | 5/1996 | Peterson et al. | |
| 5,527,288 A | 6/1996 | Gross et al. | |
| 5,569,189 A | 10/1996 | Parsons | |
| 5,599,302 A | 2/1997 | Lilley et al. | |
| 5,631,287 A | 5/1997 | Schneider | |
| 5,649,912 A | 7/1997 | Peterson | |
| 5,688,819 A | 11/1997 | Woodward et al. | |
| 5,704,911 A | 1/1998 | Parsons | |
| 5,849,792 A | 12/1998 | Schneider | |

(Continued)

FOREIGN PATENT DOCUMENTS

EA 006556 B1 2/2006
EP 1 864 666 A1 12/2007

(Continued)

OTHER PUBLICATIONS

International Preliminary Report on Patentability, dated Jul. 3, 2014, in connection with Application for PCT/US2012/070581.
International Preliminary Report on Patentability, dated Sep. 23, 2008, in connection with Application No. PCT/US2007/005424.
International Search Report and Written Opinion, dated Nov. 26, 2007, in connection with Application No. PCT/US2007/005424.
Invitation to Pay Additional Fees, dated Aug. 10, 2007, in connection with PCT/US2007/005424.
International Search Report and Written Opinion, dated May 30, 2013, in connection with Application No. PCT/US2012/070581.

(Continued)

*Primary Examiner* — Zohreh Fay
(74) *Attorney, Agent, or Firm* — Wolf, Greenfield & Sacks, P.C.

(57) ABSTRACT

The present invention relates to compositions, such as bimatoprost, latanoprost and travoprost, and methods to reduce fat in the body of an individual, for example, by topical administration, injection, and/or implantation of such compositions.

18 Claims, No Drawings

(56) References Cited

U.S. PATENT DOCUMENTS

| | | | |
|---|---|---|---|
| 5,886,035 A | 3/1999 | Shirasawa et al. | |
| 5,889,052 A | 3/1999 | Klimko et al. | |
| 5,893,397 A | 4/1999 | Peterson et al. | |
| 5,993,412 A | 11/1999 | Deily et al. | |
| 6,235,781 B1 | 5/2001 | Weiner et al. | |
| 6,262,105 B1 | 7/2001 | Johnstone | |
| 6,403,649 B1 | 6/2002 | Woodward et al. | |
| 6,646,001 B2 | 11/2003 | Hellberg et al. | |
| 6,730,707 B2 | 5/2004 | Pintor et al. | |
| 6,864,282 B2 | 3/2005 | Ling et al. | |
| 6,911,474 B2 | 6/2005 | Piomelli et al. | |
| 6,933,289 B2 | 8/2005 | Lyons et al. | |
| 7,070,768 B2 | 7/2006 | Krauss | |
| 7,125,542 B2 | 10/2006 | Miller et al. | |
| 7,351,404 B2 | 4/2008 | Woodward et al. | |
| 7,666,912 B2 | 2/2010 | Grosskreutz et al. | |
| 8,273,362 B2 | 9/2012 | Philips et al. | |
| 8,426,471 B1 | 4/2013 | Kalayoglu et al. | |
| 8,569,376 B2 | 10/2013 | Kalayoglu et al. | |
| 8,778,981 B2 | 7/2014 | Kalayoglu et al. | |
| 8,829,050 B2 | 9/2014 | Grosskreutz et al. | |
| 8,877,807 B2 | 11/2014 | Grosskreutz et al. | |
| 9,040,584 B2 | 5/2015 | Singer et al. | |
| 9,089,579 B2 | 7/2015 | Kalayoglu | |
| 9,144,574 B2 | 9/2015 | Grosskreutz | |
| 9,180,130 B2 | 11/2015 | Kalayoglu et al. | |
| 2003/0181354 A1 | 9/2003 | Abdulrazik | |
| 2004/0023954 A1 | 2/2004 | Ling et al. | |
| 2004/0082660 A1 | 4/2004 | Ueno | |
| 2004/0115234 A1 | 6/2004 | Gewirtz | |
| 2005/0058614 A1 | 3/2005 | Krauss | |
| 2005/0261373 A1 | 11/2005 | Ueno | |
| 2007/0224246 A1 | 9/2007 | Hughes et al. | |
| 2008/0015257 A1 | 1/2008 | Grosskreutz et al. | |
| 2008/0107738 A1 | 5/2008 | Philips et al. | |
| 2010/0104654 A1 | 4/2010 | Robinson et al. | |
| 2010/0105771 A1 | 4/2010 | deLong et al. | |
| 2010/0234466 A1 | 9/2010 | Grosskreutz et al. | |
| 2012/0295972 A1 | 11/2012 | Woodward et al. | |
| 2013/0178525 A1 | 7/2013 | Kalayoglu et al. | |
| 2014/0045933 A1 | 2/2014 | Kalayoglu | |
| 2014/0163098 A1 | 6/2014 | Grosskreutz et al. | |
| 2014/0350104 A1 | 11/2014 | Kalayoglu et al. | |
| 2015/0025150 A1 | 1/2015 | Kalayoglu | |
| 2015/0025151 A1 | 1/2015 | Grosskreutz et al. | |
| 2015/0105462 A1 | 4/2015 | Singer et al. | |
| 2015/0231251 A1 | 8/2015 | Singer et al. | |
| 2015/0359801 A1 | 12/2015 | Grosskreutz et al. | |

FOREIGN PATENT DOCUMENTS

| | | |
|---|---|---|
| EP | 2 228 058 A1 | 9/2010 |
| KR | 20140043562 A | 10/2014 |
| WO | WO 97/13537 A1 | 4/1997 |
| WO | WO 97/37705 A1 | 10/1997 |
| WO | WO 99/34850 A1 | 7/1999 |
| WO | WO 03/066008 A1 | 8/2003 |
| WO | WO 2005/034889 A2 | 4/2005 |
| WO | WO 2005/034890 A2 | 4/2005 |
| WO | WO 2007/111806 A2 | 10/2007 |
| WO | WO 2012/099942 A2 | 7/2012 |
| WO | WO 2012/131734 A1 | 10/2012 |

OTHER PUBLICATIONS

International Search Report and Written Opinion, dated Sep. 29, 2014, in connection with Application No. PCT/US2014/038067.
International Search Report and Written Opinion, dated Dec. 4, 2014, in connection with Application No. PCT/US2014/037512.
Invitation to Pay Additional Fees, dated Aug. 21, 2014, in connection with Application No. PCT/US2014/037512.
Extended European Search Report, dated Jul. 8, 2014, in connection with Application No. EP 12736090.7.
International Preliminary Report on Patentability, dated Aug. 1, 2013, in connection with Application for PCT/US2012/021692.
International Search Report and Written Opinion, dated May 3, 2013, in connection with Application for PCT/US2012/021692.
Invitation to Pay Additional Fees, dated Feb. 21, 2013, in connection with PCT/US2012/021692.
Extended European Search Report, dated Jul. 10, 2015, in connection with Application No. EP 12859422.3.
International Preliminary Report on Patentability, dated Nov. 19, 2015, in connection with Application No. PCT/US2014/037512.
International Search Report and Written Opinion, dated Aug. 12, 2015, in connection with Application No. PCT/US2015/037323.
Extended European Search Report, dated Dec. 21, 2015, in connection with Application No. EP 15180363.2.
International Preliminary Report on Patentability, dated Nov. 26, 2015, in connection with Application No. PCT/US2014/038067.
Second Written Opinion, dated Jun. 17, 2016, in connection with Application No. PCT/US2015/037323.
[No Author Listed], Adrenal Disorders: Cushing Syndrome. Merck Manual Professional. Last revised Nov. 2007. Available at http://www.merck.com/mmpe/sec12/ch153/ch153e.html. Last visited Dec. 22, 2008.
[No Author Listed], Allergan Announces FDA Approval of LUMIGAN as First-Line Treatment for Elevated Eye Pressure in Open-Angle Glaucoma; Indication Expands Approved Uses of LUMIGAN in the Management of Glaucoma. Business Wire. Jun. 23, 2006. Available at http://findarticles.com/p/articles/mi_m0EIN/is_2006June_23/ai_n26905641. Last visited Aug. 7, 2008. 2 pages.
[No Author Listed], Allergan Announces FDA Approval of Lumigan® as First-Line Treatment for Elevated Eye Pressure in Open-Angle Glaucoma; Indication Expands Approved Uses of Lumigan(R) in the Management of Glaucoma. Allergan Press Release. Jun. 23, 2006. Avaiable at http://agn360.client.shareholder.com/releasedetail.cfm?ReleaseID=201809. Last visited Sep. 9, 2008. 3 pages.
[No Author Listed], Chapter 42. Pharmacology of Eicosanoids. In: Principles of Pharmacology. The Pathophysiologic Basis of Drug Therapy. 3rd ed. Golan et al., eds. 2012: 743.
[No Author Listed], Dexamethasone Crystalline Product Information, Sigma Prod. No. D1756, dated Mar. 2001. 2 pages.
[No Author Listed], Excerpts from BodybuildingForYou—Bodybuilding Forums: Anabolic Steroids/Prohormones, and Testosterone Enhancers <http://www.bodybuildingforyou.com/forums/anabolic-steroids- prohormones-testosterone-enhancers/>/ Anabolic Steroids & Anabolic Chemistry & Testosterone Enhancers <http://www.bodybuildingforyou.com/forums/anabolic-steroids- anabolic-chemistry-testosterone-enhancers/>/ Anabolic Steroid, HGH, IGF, Insulin and Ancillary Profiles, pgf2a parts 3-5, post Nos. 35-37 by RRAdam on Jul. 12, 2005, http://www.bodybuildingforyou.com/forums/anabolic-steroids-anabolic-chemistry-testosterone-enhancers/22591-anabolic-steroid-hgh-igf-insulin-ancillary-profiles-2.html (14 pages).
[No Author Listed], Excerpts from Wanna Be Big Bodybuilding and Weightlifting Forums: Community Central <http://www.wannabebigforums.com/archive/index.php/f-20.html>/ General Chat <http://www.wannabebigforums.com/archive/index.php/f-12.html>/The Myostatin Gene, posted at 4:22pm, Feb. 5, 2001, by Cackerot69, http://www.wannabebicforums.com/archive/index.php/t-359.html (4 pages).
[No Author Listed], FDA CDER Approval Letter (3 pages) and Toxicology Study #5 from CDER Pharmacology Review (cover page and pp. 43-44 of 107 included) for Lumigan (Bimatoprost Ophthalmic Solution), NDA Application No. 21-275 (FDA Approval Date: Mar. 16, 2001), available at http://www.fda.gov/cder/foi/nda/2001/21275_Lumigan.htm (last visited May 23, 2008).
[No Author Listed], FDA CDER Toxicology Study #18 from CDER Pharmacology Review (cover page and pp. 67-69 of 107 included) for Lumigan (Bimatoprost Ophthalmic Solution), NDA Application No. 21-275 (FDA Approval Date: Mar. 16, 2001), available at http://www.fda.gov/cdergoi/nda/2001/21275_Lumigan.htm (last visited Dec. 22, 2008).

(56) References Cited

OTHER PUBLICATIONS

[No Author Listed], KEGG Database, Eicosanoids—Reference Pathway, available at http://www.genome.jp/kegg/pathway/map/map07034.html (last visited Jun. 10, 2008, 1 page).

[No Author Listed], Kegg Drug: D02724, [online] retrieved on Nov. 30, 2007, (2007), retrieved from http://www.genome.ad.jp/dbget-bin/www_bget?drug+D02724 and http://www.genome.ad.jp/dbget-bin/www_bget?pathway+map07035, printed page 1 and printed pp. 1-3, respectively.

[No Author Listed], Latisse and Safety. Last accessed on Jul. 24, 2012 at http://www.latisseonline.com/latisse-safety/ 2 pages.

[No Author Listed], Material Safety Data Sheet for LUTALYSE® Sterile Solution, dated Jun. 23, 1997, available at httplApfvww.lutelysacomipahirnageslmsde...usiLutalvse.pdf (last visited Dec. 22, 2006).

[No Author Listed], Original New Animal Drug Application for ProstaMateTm (dinoprost tromethamine injection) Sterile Solution (ANADA No. 200-253). Dated Feb. 12, 1999. Available at http://www.fdagovlohrmsidockets/98fr1200253fi.pdf. Last visited Dec. 22, 2008.

[No Author Listed], Pfizer Inc., Citizen Petition to the Food and Drug Administration: Revoke Approval of Allergan's Supplemental NDA #21-257/S-013 for Lumigan (Bimatoprost Ophthalmic Solution 0.03%) and Deny Alcon's Supplemental NDA for Travatan (Travoprost Ophthalmic Solution 0.004%), submitted on Nov. 1, 2006, available at http://www.fda.gov/ohrms/dockets/dockets/06p0450/06p-0450-cp00001-toc.htm.

[No Author Listed], Prescribing Information for SAFLUTAN® 15 micrograms/ml eye drops, solution, single-dose container (tafluprost), dated Aug. 2009.

[No Author Listed], Product label of DECADRON® dexamethasone tablets, label for May 17, 2004 approval (NDA No. 011664), available at http://dailymed.nlm.nih.gov/dailvmed/druulnfo.cfm?id=2934 (last visitedDec. 22, 2008).

[No Author Listed], Product Label of LUMIGAN (bimatoprost ophthalmic solution) 0.03%, label for Jun. 22, 2006 approval of new or modified indication, available at http://www.fda.gov/cder/foi/label/2006/021275s013lbl.pdf (last visited Sep. 9, 2008).

[No Author Listed], Product Label of TRAVATAN® (travoprost ophthalmic solution) 0.004%, label for Feb. 13, 2003 approval of efficacy supplement with clinical data to support, available at http://www.fda.gov/cder/foUlabe1/2003/021257s0061bl.pdf (last visited Sep. 9, 2008).

[No Author Listed], Product Label of Xalatan® (latanoprost ophthalmic solution), label for Dec. 20, 2002 approval of new or modified indication, available at http://www.fda.gov/cder/foi/label/2002/20597SE1-010_Xalatan_lbl.pdf (last visited Sep. 9, 2008).

[No Author Listed], Prostaglandin analogues. Entrepreneur.com. 2008. Available at http://www.entrepreneur.com/tradejournals/article/print/166777491.html. 2 pages.

[No Author Listed], The American Heritage® Dictionary of the English Language, Fourth Edition, 2000, p. 1701 (with the definition of "steroid").

[No Author Listed], TRAVATAN™ (travoprost ophthalmic solution) 0.004% Sterile. NDA 21-257. Alcon Laboratories Inc. 2001. 7 pages.

Aihara et al., Incidence of deepening of the upper eyelid sulcus after switching from latanoprost to bimatoprost. Jpn J Ophthalmol. Nov. 2011;55(6):600-4. Epub Sep. 28, 2011.

Aydin et al., Recovery of orbital fat pad prolapsus and deepening of the lid sulcus from topical bimatoprost therapy: 2 case reports and review of the literature. Cutan Ocul Toxicol. Sep. 2010;29(3):212-6.

Baer et al., Measurement of body composition of live rats by electromagnetic conductance. Physiol Behav. Jun. 1993;53(6):1195-9.

Berge et al., Pharmaceutical salts. J Pharm Sci. Jan. 1977;66(1):1-19.

Bertin et al., Evaluation of dual-energy X-Ray absorptiometry for body-composition assessment in rats. J Nutr. Sep. 1998;128(9):1550-4.

Blank et al., Mechanism of percutaneous absorption. 3. The effect of temperature on the transport of non-electrolytes across the skin. J Invest Dermatol. Dec. 1967;49(6):582-9.

Casimir et al., Preadipocyte differentiation blocked by prostaglandin stimulation of prostanoid FP2 receptor in murine 3T3-L1 cells. Differentiation. Jul. 1996;60(4):203-10.

Casimir, Regulation of early preadipocyte differentiation: cAMP and prostaglandin F-2-alpha. ProQuest Dissertations and Theses; 1996; ProQuest Dissertations & Theses (PQDT). UMI No. 9634889. 162 pages.

Chapman et al., Glucocorticoid regulation of adipocyte differentiation: hormonal triggering of the developmental program and induction of a differentiation-dependent gene. J Cell Biol. Oct. 1985;101(4):1227-35.

Choi et al., In vitro study of antiadipogenic profile of latanoprost, travoprost, bimatoprost, and tafluprost in human orbital preadiopocytes. J Ocul Pharmacol Ther. Apr. 2012;28(2):146-52. Epub Nov. 22, 2011. E-pub version.

Culebras et al., Total Body Water and the Exchangeable Hydrogen. II. Total body water and the exchangeable hydrogen. II. A review of comparative data from animals based on isotope dilution and desiccation, with a report of new data from the rat. Am J Physiol. Jan. 1977;232(1):R60-5.

Dahms et al., Correlation of percent body fat with body specific gravity in rats. J Nutr. Feb. 1982;112(2):398-400.

Database WPI, Week 201434. Thomson Scientific, London, GB; AN 2014-G76718 XP002729483 & KR 2014 0043562. Apr. 10, 2014. 3 pages.

Email from Dr. Louis Pasquale to Lisa Putukian sent at 10:16 am, May 20, 2008, and forwarded to Daniel Wilson at 10:22 am, May 20, 2008, and related e-mail thread (3 pages).

E-mail from Dr. Michael Singer to Randall Morin sent at 1:57 pm, Jun. 4, 2008, and attached letter (8 pages) and Exhibits 1-10 from Dr. Singer to Mr. Morin dated Jun. 4, 2004.

Ettmayer et al., Lessons learned from marketed and investigational prodrugs. J Med Chem. May 6, 2004;47(10):2393-404.

Filippopoulos et al., Periorbital changes associated with topical bimatoprost. Ophthal Plast Reconstr Surg. Jul.-Aug. 2008;24(4):302-7.

Frisch et al., Carcass components at first estrus of rats on high-fat and low-fat diets: body water, protein, and fat. Proc Natl Acad Sci U S A. Jan. 1977;74(1):379-83.

Gorin et al., Evidence for a role of protein kinase C in the stimulation of lipolysis by growth hormone and isoproterenol. Endocrinology. Jun. 1990;126(6):2973-82.

Gregoire et al., Understanding adipocyte differentiation. Physiol Rev. Jul. 1998;78(3):783-809.

Grosskreutz et al., Periorbital Fat Loss and Eyelid Sulcus Deepening after Bimatoprost Therapy. Final Program and Abstract Book, pp. 49 and 53, distributed at The American Glaucoma Society 2006 Annual Meeting, Mar. 2-5, 2006.

Grosskreutz et al., Periorbital Fat Loss and Eyelid Sulcus Deepening after Bimatoprost Therapy. Poster presented at The American Glaucoma Society 2006 Annual Meeting, Charleston, South Carolina. Mar. 2-5, 2006. 1 page.

Grosskreutz, Abstract submitted on Nov. 1, 2005 to the American Glaucoma Society for the American Glaucoma Society 2006 Annual Meeting. 1 page.

Hata et al., Pharmacology and signaling of prostaglandin receptors: multiple roles in inflammation and immune modulation. Pharmacol Ther. Aug. 2004;103(2):147-66.

Hellberg et al., The hydrolysis of the prostaglandin analog prodrug bimatoprost to 17-phenyl-trinor PGF2alpha by human and rabbit ocular tissue. J Ocul Pharmacol Ther. Apr. 2003;19(2):97-103.

Holmstrom et al., Analytic review of bimatoprost, latanoprost and travoprost in primary open angle glaucoma. Curr Med Res Opin. Nov. 2005;21(11):1875-83.

Husain et al., Acute effects of PGF2alpha on MMP-2 secretion from human ciliary muscle cells: a PKC- and ERK-dependent process. Invest Ophthalmol Vis Sci. May 2005;46(5):1706-13.

Initial Information Disclosure Statement for U.S. Appl. No. 11/712,839, May 19, 2008 (4 pages).

(56) References Cited

OTHER PUBLICATIONS

Inoue et al., Deepening of the Upper Eyelid Sulcus Caused by 5 Types of Prostaglandin Analogs. J Glaucoma. Aug. 29, 2012. [Epub ahead of print] E-pub version. 6 pages.

Izumi et al., Short-term effects of topical tafluprost on retinal blood flow in cats. J Ocul Pharmacol Ther. Oct. 2008;24(5):521-6. doi: 10.1089/jop.2007.0065.

Jabbour et al., A positive feedback loop that regulates cyclooxygenase-2 expression and prostaglandin F2alpha synthesis via the F-series-prostanoid receptor and extracellular signal-regulated kinase 1/2 signaling pathway. Endocrinology. Nov. 2005;146(11):4657-64. Epub Aug. 4, 2005.

Künnecke et al., Quantitative body composition analysis in awake mice and rats by magnetic resonance relaxometry. Obes Res. Oct. 2004;12(10):1604-15.

Lepak et al., Inhibition of adipose differentiation by 9 alpha, 11 beta-prostaglandin F2 alpha. Prostaglandins. Dec. 1993;46(6):511-7.

Lepak et al., Prostaglandin F2 alpha stimulates transforming growth factor-alpha expression in adipocyte precursors. Endocrinology. Aug. 1995;136(8):3222-9.

Lesser et al., Modification of subcutaneous adipose tissue by a methylxanthine formulation: a double-blind controlled study. Dermatol Surg. Jun. 1999;25(6):455-62.

Letter from Dr. Michael Singer to Lisa Putukian dated Sep. 22, 2008 (1 page—email correspondence attachment and MEEI Patent Policy and Procedures attachment omitted).

Letter from Dr. Michael Singer to Lisa Putukian dated Sep. 26, 2007 (3 pages and facsimile cover sheet).

Letter from Lisa Putukian to Dr. Michael Singer dated Sep. 22, 2008 (1 page.).

Letter from Lisa Putukian to Dr. Michael Singer dated Sep. 28, 2007 (2 pages), and attached Preliminary Amendment (3 pages).

Lin et al., Green tea polyphenol epigallocatechin gallate inhibits adipogenesis and induces apoptosis in 3T3-L1 adipocytes. Obes Res. Jun. 2005;13(6):982-90.

Liu et al., Postaglandin F2alpha inhibits adipocyte differentiation via a G alpha q-calcium-calcineurin-dependent signaling pathway. J Cell Biochem. Jan. 1, 2007;100(1):161-73.

Löffler et al., Adipose tissue development: the role of precursor cells and adipogenic factors. Part II: The regulation of the adipogenic conversion by hormones and serum factors. Klin Wochenschr. Sep. 1, 1987;65(17):812-7.

Maxey et al., The hydrolysis of bimatoprost in corneal tissue generates a potent prostanoid FP receptor agonist. Surv Ophthalmol. Aug. 2002;47 Suppl 1:S34-40.

Miller et al., The mechanism of inhibition of 3T3-L1 preadipocyte differentiation by prostaglandin F2alpha. Endocrinology. Dec. 1996;137(12):5641-50.

Morissette et al., High-throughput crystallization: polymorphs, salts, co-crystals and solvates of pharmaceutical solids. Adv Drug Deliv Rev. Feb. 23, 2004;56(3):275-300.

Nakajima et al., New fluoroprostaglandin F(2alpha) derivatives with prostanoid FP-receptor agonistic activity as potent ocular-hypotensive agents. Biol Pharm Bull. Dec. 2003;26(12):1691-5.

Nakakura et al., Latanoprost therapy after sunken eyes caused by travoprost or bimatoprost. Optom Vis Sci. Sep. 2011;88(9):1140-4.

Pantoja et al., Glucocorticoid signaling defines a novel commitment state during adipogenesis in vitro. Mol Biol Cell. Oct. 2008;19(10):4032-41. Epub Jul. 23, 2008.

Park et al., Changes to upper eyelid orbital fat from use of topical bimatoprost, travoprost, and latanoprost. Jpn J Ophthalmol. Jan. 2011;55(1):22-7. Epub Feb. 18, 2011.

Paula et al., Periorbital Fat Loss and Eyelid Sulcus Deepening after Bimatoprost Therapy. Manuscript submitted to Archives of Ophthalmology, Oct. 21, 2005 (10 pages).

Peplinski et al., Deepening of lid sulcus from topical bimatoprost therapy. Optom Vis Sci. Aug. 2004;81(8):574-7.

Reginato et al., Prostaglandins promote and block adipogenesis through opposing effects on peroxisome proliferator-activated receptor gamma. J Biol Chem. Jan. 23, 1998;273(4):1855-8.

Robin, An accurate comparison of bimatoprost's efficacy and adverse effects. Arch Ophthalmol. Jul. 2002;120(7):999-1000; author reply 1000.

Rundle, Drug That Lengthens Eyelashes Sets Off Flutter. Wall Street J. Nov. 19, 2007 (2 pages).

Sales et al., Expression, localization, and signaling of prostaglandin F2 alpha receptor in human endometrial adenocarcinoma: regulation of proliferation by activation of the epidermal growth factor receptor and mitogen-activated protein kinase signaling pathways. J Clin Endocrinol Metab. Feb. 2004;89(2):986-93.

Sales et al., F-prostanoid receptor regulation of fibroblast growth factor 2 signaling in endometrial adenocarcinoma cells. Endocrinology. Aug. 2007;148(8):3635-44. Epub May 3, 2007.

Schiwek et al., Glucocorticoid hormones contribute to the adipogenic activity of human serum. Endocrinology. Feb. 1987;120(2):469-74. Abstract only.

Selliah et al., AL-12182, a novel 11-oxa prostaglandin analog with topical ocular hypotensive activity in the monkey. Bioorg Med Chem Lett. Sep. 6, 2004;14(17):4525-8.

Serrero et al., Prostaglandin F2 alpha inhibits epidermal growth factor binding to cellular receptors on adipocyte precursors in primary culture. Biochem Biophys Res Commun. Jul. 26, 1995;212(3):1125-32.

Serrero et al., Prostaglandin F2 alpha inhibits the differentiation of adipocyte precursors in primary culture. Biochem Biophys Res Commun. Mar. 16, 1992;183(2):438-42.

Serrero et al., Prostaglandin F2alpha receptor (FP receptor) agonists are potent adipose differentiation inhibitors for primary culture of adipocyte precursors in defined medium. Biochem Biophys Res Commun. Apr. 7, 1997;233(1):200-2.

Shah et al., A cross-sectional survey of the association between bilateral topical prostaglandin analogue use and ocular adnexal features. PLoS One. May 1, 2013;8(5):e61638. doi: 10.1371/journal.pone.0061638. Print 2013. 7 pages.

Sharif et al., Agonist activity of bimatoprost, travoprost, latanoprost, unoprostone isopropyl ester and other prostaglandin analogs at the cloned human ciliary body FP prostaglandin receptor. J Ocul Pharmacol Ther. Aug. 2002;18(4):313-24.

Shi et al., A glucocorticoid-induced leucine-zipper protein, GILZ, inhibits adipogenesis of mesenchymal cells. EMBO Rep. Apr. 2003;4(4):374-80. Epub Mar. 14, 2003.

Shugart et al., Dexamethasone signaling is required to establish the postmitotic state of adipocyte development. Cell Growth Differ. Oct. 1997;8(10):1091-8.

Stella, Prodrugs as therapeutics. Expert Opin Ther Patents. 2004;14(3):277-80.

Tappeiner et al., [Orbital fat atrophy in glaucoma patients treated with topical bimatoprost—can bimatoprost cause enophthalmos?]. Klin Monbl Augenheilkd. May 2008;225(5):443-5. English abstract only.

Testa, Prodrug research: futile or fertile? Biochem Pharmacol. Dec. 1, 2004;68(11):2097-106.

Tsuboi et al., Prostanoid EP4 receptor is involved in suppression of 3T3-L1 adipocyte differentiation. Biochem Biophys Res Commun. Sep. 24, 2004;322(3):1066-72.

Vippagunta et al., Crystalline solids. Adv Drug Deliv Rev. May 16, 2001;48(1):3-26.

Wolff et al., Burger's Medicinal Chemistry and Drug Discovery. Fifth Edition. vol. I: Principles and Practice. 1994:975-7.

Woodward et al., Prostamides (prostaglandin-ethanolamides) and their pharmacology. Br J Pharmacol. Feb. 2008;153(3):410-9. Epub Aug. 27, 2007.

Woodward et al., The pharmacology of bimatoprost (Lumigan™). Surv Ophthalmol. May 2001;45 Suppl 4:S337-45.

Yam et al., Bilateral deepening of upper lid sulcus from topical bimatoprost therapy. J Ocul Pharmacol Ther. Oct. 2009;25(5):471-2.

Ziegler, FDA Approves Latisse Eyelash Growth Product. Last accessed Jul. 24, 2012 at http://voices.yahoo.com/fda-approves-latisse-eyelash-growth-product-3520905.html?cat=39. 3 pages.

(56) References Cited

OTHER PUBLICATIONS

U.S. Appl. No. 12/652,968, filed Jan. 6, 2010, Grosskreutz et al.
U.S. Appl. No. 13/548,482, filed Jul. 13, 2012, Kalayoglu et al.
U.S. Appl. No. 13/782,659, filed Mar. 1, 2013, Kalayoglu et al.
U.S. Appl. No. 14/363,923, filed Jun. 9, 2014, Kalayoglu et al.
U.S. Appl. No. 14/932,445, filed Nov. 4, 2015, Kalayoglu et al.
U.S. Appl. No. 14/889,093, filed Nov. 4, 2015, Singer et al.
U.S. Appl. No. 14/575,873, filed Dec. 18, 2014, Kalayoglu et al.
U.S. Appl. No. 14/702,365, filed May 1, 2015, Kalayoglu et al.
U.S. Appl. No. 13/980,179, filed Oct. 18, 2013, Kalayoglu.
U.S. Appl. No. 14/509,680, filed Oct. 8, 2014, Kalayoglu.

COMPOSITIONS AND METHODS FOR REDUCING BODY FAT

CROSS-REFERENCE TO RELATED APPLICATIONS

The present application is a continuation of and claims priority under 35 U.S.C. §120 to U.S. application Ser. No. 14/838,049, filed Aug. 27, 2015, now U.S. Pat. No. 9,421,215, which is a continuation of and claims priority under 35 U.S.C. §120 to U.S. application Ser. No. 14/504,788, filed Oct. 2, 2014, now U.S. Pat. No. 9,144,574, which is a continuation of and claims priority under 35 U.S.C. §120 to U.S. application Ser. No. 14/180,074, filed Feb. 13, 2014, now U.S. Pat. No. 8,877,807, which is a continuation of and claims priority under 35 U.S.C. §120 to U.S. application Ser. No. 12/652,968, filed Jan. 6, 2010, now U.S. Pat. No. 8,829,050, which is a continuation of and claims priority under 35 U.S.C. §120 to U.S. application Ser. No. 11/712,839, filed Mar. 1, 2007, now U.S. Pat. No. 7,666,912, which claims the benefit of and priority to U.S. Provisional Patent application Ser. No. 60/785,360, filed Mar. 23, 2006, and U.S. Provisional Patent application Ser. No. 60/844,337, filed Sep. 13, 2006, the entire disclosures of which are incorporated by reference herein for all purposes.

FIELD OF THE INVENTION

The present invention relates generally to compounds and methods for reducing fat in the body of an individual. More specifically, body fat may be reduced by administering compounds identified as cyclopentane heptanoic acid, 2-cycloalkyl or arylalkyl compounds and derivatives thereof.

BACKGROUND

Excess body fat, which may be diffuse or concentrated on particular parts of the body, plays an important role in a wide array of human diseases. For many people excess body fat is also a source of psychosocial distress and reduced self-esteem. As one form of excess body fat, obesity is responsible for much of the morbidity and health care costs in the United States. It is known to be a risk factor for type 2 diabetes, hypertension, hyperlipidemia, coronary artery disease, stroke, breast and colon cancer, sleep apnea, gallbladder disease, gastroesophogeal reflux disease, fatty liver, gout, and thromboembolism. Levels of cholesterol, blood pressure, blood sugar and uric acid are usually higher in obese people than in those of normal weight. Overweight people also display increased morbidity from coronary heart disease. Despite increased awareness of these health risks among Americans, the prevalence of obesity in the United States has more than doubled since the turn of the century. As a result, there has been considerable interest in methods to reduce obesity.

Another problem, which may exist with or without obesity, is excess body fat concentrated on particular portion(s) of the body. This may involve, for example, prominent and undesired deposits of fat on the abdomen, buttocks, thighs, arms, and/or chin. Such local accumulations of body fat (alternatively known as fat maldistribution) may result from disease, hormonal status, or as side effects of medication or other substances. Even in the absence of disease, cosmetic considerations apply to individuals who nevertheless perceive an excess or maldistribution of fat and wish to have it corrected.

A number of medical conditions are also associated with obesity or local excesses of body fat. These include Cushing syndrome, pseudo-Cushing syndrome, drug-induced obesity, HIV-related lipodystrophy, hypothyroidism, pseudohypoparathyroidism, hypothalamic obesity, polycystic ovarian disease, depression, binge eating, Prader-Willi syndrome, Bardet-Biedl syndrome, Cohen syndrome, Down syndrome, Turner syndrome, growth hormone deficiency, growth hormone resistance, and leptin deficiency or resistance.

Medications known to cause obesity or local excesses of body fat include cortisol and analogs, other corticosteroids, megace, sulfonylureas, antiretrovirals, trycyclic antidepressants, monoamine oxidase inhibitors, selective serotonin reuptake inhibitors, oral contraceptives, insulin, risperidone, clozapine, and thiazolidinediones. Some of these medications, such as cortisol and antiretrovirals, can cause profound fat maldistribution with characteristics such as "moon facies" and a "buffalo hump."

Changes in hormonal status, including physiologic changes such as pregnancy or menopause, may result in excess body fat. Smoking cessation commonly leads to weight gain and excess body fat. Trauma may favor the accumulation of excess body fat by virtue of immobility or disuse of an extremity. Similar problems may affect astronauts or anybody immobilized for extended periods of time. Some tumors, most notably lipomas, are characterized by local collections of fatty cells that may be amenable to methods used to treat other concentrations of body fat.

A number of diseases that do not involve excess fat may nevertheless benefit from methods to reduce fat deposits. For example, although thyroid orbitopathy (Grave's disease) is not primarily a result of excess orbital fat, one treatment is to debulk the orbital fat. Those who have suffered hip fractures, for example, show improved outcomes with weight loss. A number of plastic surgery procedures would benefit from adjunctive methods to reduce fat deposits.

Even in the absence of underlying pathology, an individual may have cosmetic concerns about local or diffuse deposits of body fat. These can usually be attributed to constitutional or hereditary factors, developmental history, age, gender, diet, alcohol use, or other components of lifestyle. Individuals in such circumstances commonly wish to reduce the amount of fat on the abdomen, chest, buttocks, hips, thighs, legs, knees, arms, chin, and/or neck. Others may wish to modify facial or orbital fat, as in somebody with prominent facial fat pads or orbital fat prolapse.

A number of methods have been developed to reduce or remove excess body fat. It is helpful to classify these methods as either extractive or metabolic. Extractive methods, such as lipoplasty (liposuction) or local excision, are methods whereby fat is mechanically removed from areas of interest. Such methods enable one to focus on particular parts of the body; however, they are costly and may involve scars, postsurgical deformity or regression, discomfort, and adverse reactions.

In contrast to extractive methods, metabolic methods, which include medications, nutritional supplements, devices, and exercise or other body treatment, seek to modify the body's metabolism (whether caloric consumption, expenditure, or both) such that the body incurs a net loss of fat. Such methods reduce overall body fat but are not particularly suitable for those who wish to remove body fat from particular areas of the body. Another disadvantage is potential concomitant loss of water, carbohydrates, protein, vitamins, minerals, and/or other nutrients. Furthermore, when such methods involve medications, they tend to affect the entire body. Such medications may have undesired side effects, for example palpitations, tremor, insomnia, and irritability in those who use stimulants as appetite suppressants. Despite obvious salubrious value, the traditional metabolic methods of diet and exercise are not practical for everybody.

Therefore, there is a need for new methods and compositions for reducing the body fat of individuals.

SUMMARY OF THE INVENTION

The present invention describes the use of certain cyclopentane heptanoic acid, 2-cycloalkyl, or arylalkyl compounds and derivatives thereof, such as bimatoprost, to reduce, or eliminate altogether, body fat, for example, adipose tissue in a mammal, for example, a human. These compounds have been described previously, for example in U.S. Pat. Nos. 5,688,819 and 6,403,649. However, it has now been discovered that these compounds can be used to reduce body fat.

Accordingly, in one aspect the invention provides a method for reducing fat in a body of an individual, the method including administering to the skin of a body, injecting into a fat deposit of a body, and/or implanting an implantable depot into a body, in an amount sufficient to reduce fat in the body, a compound of formula I

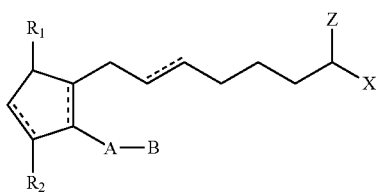

in which the dashed bonds represent a single or double bond which can be in the cis or trans configuration; A is alkylene or alkenylene radical having from two to six carbon atoms, which radical may be interrupted by one or more oxide radicals and substituted with one or more hydroxy, oxo, alkyloxy or alkylcarboxy groups, in which the alkyl radical can be from one to six carbon atoms; B is a cycloalkyl radical having from three to seven carbon atoms or an aryl radical selected from the group consisting of hydrocarbyl aryl and heteroaryl radicals having from four to ten carbon atoms in which a heteroatom may be selected from the group consisting of nitrogen, oxygen and sulfur atoms; X is a radical selected from the group consisting of $-OR^4$ and $-N(R^4)_2$ in which $R^4$ is selected from the group consisting of hydrogen, a lower alkyl radical having from one to six carbon atoms, and

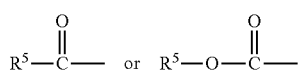

in which $R^5$ is a lower alkyl radical having from one to six carbon atoms; Z is $=O$ or represents 2 hydrogen radicals; one of $R_1$ and $R_2$ is $=O$, $-OH$, or a $-O(CO)R_6$ group and the other one is $-OH$ or $-O(CO)R_6$, or $R_1$ is $=O$ and $R_2$ is H, in which $R_6$ is a saturated or unsaturated acyclic hydrocarbon group having from 1 to about 20 carbon atoms or $-(CH_2)_m R_7$ in which m is 0-10 and $R_7$ is cycloalkyl radical having from three to seven carbon atoms, or a hydrocarbyl aryl or heteroaryl radical, as defined above, or a pharmaceutically-acceptable salt thereof, optionally provided however that when B is not substituted with a pendant heteroatom-containing radical and Z is $=O$, then X is not $-OR^4$.

In certain embodiments, the invention provides a method for reducing fat in a body of an individual, the method including administering to the skin of a body, injecting into a fat deposit of a body, and/or implanting into a body an implantable depot in an amount sufficient to reduce fat in the body, a compound represented by formula II

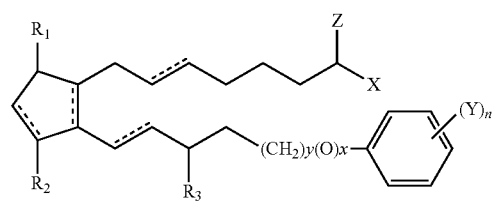

in which y is 0 or 1, x is 0 or 1 and x and y are not both 1; Y is a radical selected from the group consisting of alkyl, halo, nitro, amino, thiol, hydroxy, alkyloxy, alkylcarboxy and halosubstituted alkyl, in which the alkyl radical can be from one to six carbon atoms, n is 0 or an integer of from 1 to 3 and $R_3$ is $=O$, $-OH$ or $-O(CO)R_6$, and pharmaceutically acceptable salts thereof. In certain circumstances, formula II can be considered an embodiment of formula I.

In certain embodiments, the invention provides a method for reducing fat in a body of an individual, the method including administering to the skin of a body, injecting into a fat deposit of a body, and/or implanting into a body an implantable depot in an amount sufficient to reduce fat in the body, a compound represented by formula III

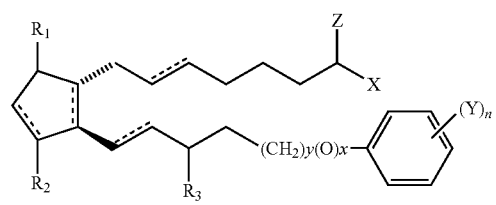

in which hatched lines indicate the α configuration and solid triangles indicate the β configuration, and pharmaceutically acceptable salts thereof. In certain circumstances, formula III can be considered an embodiment of formula II.

In certain embodiments, the invention provides a method for reducing fat in a body of an individual, the method including administering to the skin of a body, injecting into a fat deposit of a body, and/or implanting into a body an implantable depot in an amount sufficient to reduce fat in the body, a compound represented by formula IV

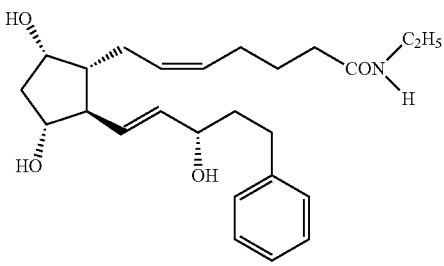

and pharmaceutically acceptable salts thereof. In certain circumstances, formula IV can be considered an embodiment of formula III.

In certain embodiments, the invention provides a method for reducing fat in a body of an individual, the method including administering to the skin of a body, injecting into a fat deposit of a body, and/or implanting into a body an implantable depot in an amount sufficient to reduce fat in the body, a compound represented by formula VII

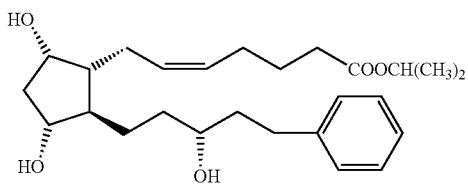

and pharmaceutically acceptable salts thereof. In certain circumstances, formula VII can be considered an embodiment of formula III.

In certain embodiments, the invention provides a method for reducing fat in a body of an individual, the method including administering to the skin of a body, injecting into a fat deposit of a body, and/or implanting into a body an implantable depot in an amount sufficient to reduce fat in the body, a compound represented by formula VIII

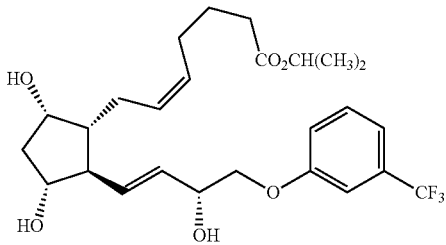

and pharmaceutically acceptable salts thereof. In certain circumstances, formula VIII can be considered an embodiment of formula III.

In certain embodiments, the invention provides a method for reducing fat in a body of an individual, the method including administering to the skin of a body, injecting into a fat deposit of a body, and/or implanting into a body an implantable depot in an amount sufficient to reduce fat in the body, a compound represented by formula V

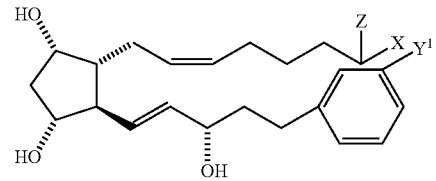

in which hatched lines indicate the α configuration and solid triangles indicate the β configuration, and in which $Y^1$ is Cl or trifluoromethyl, and pharmaceutically acceptable salts thereof. In certain circumstances, formula V can be considered an embodiment of formula I.

In certain embodiments, the invention provides a method for reducing fat in a body of an individual, the method including administering to the skin of a body, injecting into a fat deposit of a body, and/or implanting into a body an implantable depot in an amount sufficient to reduce fat in the body, a compound represented by formula VI

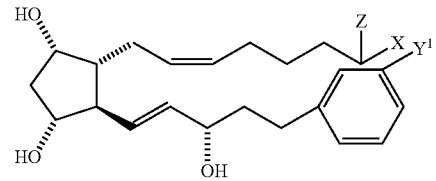

in which $Y^1$ is Cl or trifluoromethyl, and the position 9- and/or 11- and/or 15-esters of the compound, and pharmaceutically acceptable salts thereof. This is embodiment can have the following features. Z can be =O and X can be $NH_2$ or an amido radical. X can be selected from the group consisting of $NH_2$ and $OCH_3$. In certain circumstances, formula VI can be considered an embodiment of formula I.

In certain embodiments, the compound can be cyclopentane heptenol-5-cis-2-(3α-hydroxy-5-phenyl-1-trans-pentenyl)-3,5-dihydroxy, [$1_\alpha$, $2_\beta$, $3_\alpha$, $5_\alpha$]; cyclopentane heptenamide-5-cis-2-(3α-hydroxy-5-phenyl-1-trans-pentenyl)-3,5-dihydroxy, [$1_\alpha$, $2_\beta$, $3_\alpha$, $5_\alpha$]; cyclopentane N,N-dimethylheptenamide-5-cis-2-(3α-hydroxy-5-phenyl-1-trans-pentenyl)-3,5-dihydroxy, [$1_\alpha$, $2_\beta$, $3_\alpha$, $5_\alpha$]; cyclopentane heptenyl methoxide-5-cis-2-(3α-hydroxy-5-phenyl-1-trans-pentenyl)-3, 5-dihydroxy, [$1_\alpha$, $2_\beta$, $3_\alpha$, $5_\alpha$]; cyclopentane heptenyl ethoxide-5-cis-2-(3α-hydroxy-4-meta-chlorophenoxy-1-trans-pentenyl)-3,5-dihydroxy, [$1_\alpha$, $2_\beta$, $3_\alpha$, $5_\alpha$]; cyclopentane heptenylamide-5-cis-2-(3α-hydroxy-4-meta-chlorophenoxy-1-trans-pentenyl)-3,5-dihydroxy, [$1_\alpha$, $2_\beta$, $3_\alpha$, $5_\alpha$]; cyclopentane heptenylamide-5-cis-2-(3α-hydroxy-4-trifluoromethylphenoxy-1-trans-pentenyl)-3,5-dihydroxy, [$1_\alpha$, $2_\beta$, $3_\alpha$, $5_\alpha$]; cyclopentane N-isopropyl heptenamide-5-cis-2-(3α-hydroxy-5-phenyl-1-trans-pentenyl)-3,5-dihydroxy, [$1_\alpha$, $2_\beta$, $3_\alpha$, $5_\alpha$]; cyclopentane N-methyl heptenamide-5-cis-2-(3α-hydroxy-5-phenyl-1-trans-pentenyl)-3,5-dihydroxy, [$1_\alpha$, $2_\beta$, $3_\alpha$, $5_\alpha$]; cyclopentane heptenol-5-cis-2-(3α-hydroxy-4-meta-chlorophenoxy-1-trans-butenyl)-3,5-dihydroxy, [$1_\alpha$, $2_\beta$, $3_\alpha$, $5_\alpha$]; cyclopentane heptenamide-5-cis-2-(3α-hydroxy-4-meta-chlorophenoxy-1-trans-butenyl)-3,5-dihydroxy, [$1_\alpha$, $2_\beta$, $3_\alpha$, $5_\alpha$]; and/or cyclopentane heptenol-5-cis-2-(3α-hydroxy-5-phenyl-1-trans-pentenyl)3,5-dihydroxy, [$1_\alpha$, $2_\beta$, $3_\alpha$, $5_\alpha$].

Further features of any of the above-identified aspects and/or embodiments include the following. Fat reduction can occur at a localized area, in which the localized area can include the abdomen, chest, buttocks, hips, thighs, legs, knees, arms, chin, neck, face, and combinations thereof. The individual can have excess body fat as a side effect of medication, in which the medication can include a corticosteroid, an antidepressant, and/or a form of insulin. The individual can be suffering from a condition such as excess body weight, obesity, fat maldistribution syndrome, HIV, a genetic disorder characterized at least in part by excess body fat, Grave's disease, diabetes mellitus, present or recent smoking cessation, and combinations thereof. A method can further include performing a cosmetic or surgical procedure, in which the procedure can include mammoplasty, blepharoplasty, abdominoplasty, lipoplasty, liposuction, rhinoplasty, botulinum toxin administration, transverse rectus abdominis muscle flap, orbital decompression, midface lift, sub-orbicularis oculi fat lift, brow lift, and combinations thereof.

For methods including administering one or more of the compounds to the skin of a body, the compound can be delivered in forms including an ointment, a lotion, a cream, a patch, a transdermal system, or combinations thereof. For methods including administering one or more of the compounds by injection, the compound can include a subcutaneous injection, an intramuscular injection, an intralesional injection, or combinations thereof. For any of the methods described above, one or more compounds can be delivered in a sustained-release formulation.

In any aspect and/or embodiment of the invention, the individual can be a mammal and the mammal can be a human. Fat reduction can include reducing fat as measured by at least one of volume, size, mass, bulk, density, amount, and/or quantity. Local and/or total fat reduction can be greater than or equal to 50 percent, greater than or equal to 25 percent, greater than or equal to 10 percent, or greater than or equal to 5 percent. Fat reduction can include reducing fat cell amount (for example, fat cell number), reducing fat cell volume, reducing fat cell maturation, and/or dedifferentiating a fat cell.

The foregoing aspects and embodiments of the invention may be more fully understood by reference to the following detailed description and claims.

DETAILED DESCRIPTION OF THE INVENTION

The present invention describes novel uses of certain cyclopentane heptanoic acid, 2-cycloalkyl or arylalkyl compounds and derivatives thereof, such as bimatoprost, to reduce, or eliminate altogether, body fat, for example, adipose tissue, in a mammal, for example, a human. Previously, these compounds were recognized as hypotensive agents (for example, U.S. Pat. Nos. 5,688,819 and 6,403,649). Specifically, these compounds were shown to effect vasodilation and thereby were predicted to relieve symptoms of various diseases associated with increased pressure, including acute myocardial infarction, vascular thrombosis, hypertension, pulmonary hypertension, ischemic heart disease, congestive heat failure, and angina pectoris. Specifically, these compounds were shown to be effective ocular hypotensive agents useful for the treatment of various ocular hypertensive conditions, including post-surgical trabeculectomy ocular hypertensive episodes, post laser trabeculoplasty ocular hypertensive episodes, and glaucoma. Glaucoma is a disease of the eye characterized by optic nerve degeneration, most commonly induced by elevated intraocular pressure.

Previous studies have shown that the use of bimatoprost eyedrops for the treatment of glaucoma does decrease intraocular pressure, but it also induces unwanted side-effects including periocular pigmentary changes involving the eyelid and deepening of the lid sulcus of the eye that receives the bimatoprost eye drops. (Peplinski et al. (2004) OPTOM. VIS. SCI. 81:574-577). It was previously theorized that the unwanted side-effect of lid sulcus deepening as a function of topical bimatoprost administration to the eye was caused by a change to Mueller's muscle, however, it was recognized that further investigation would be needed to understand the cause of this unwanted side-effect. (Peplinski (2004)).

The present invention involves the recognition that the unwanted side-effect of lid sulcus deepening as a function of topical bimatoprost administration to the eye is caused by a decease in fat surrounding the eye. Because of this recognition, the present invention extends the use of one or more cyclopentane heptanoic acid, 2-cycloalkyl or arylalkyl compounds and derivatives thereof, including bimatoprost, to reduce fat in body of an individual. An individual may use one or more of these compounds to reduce body fat from a particular part of the body, and this may be accomplished without systemic administration and with minimal if any side effects. These compounds may be administered by an individual to himself or herself repeatedly and without special equipment or training, although a medical professional also can administer such compounds. Daily administration may be adequate (but not necessarily preferable) to achieve the desired effect, such that the schedule of administration would be convenient.

Without being bound by theory, reduction in fat as a function of administration of bimatoprost and/or or one or more other cyclopentane heptanoic acid, 2-arylalkyl or cycloalkyl compounds or derivatives thereof may include reducing the number of fat cells, reducing the volume of one or more fat cells, reducing maturation of one or more fat cells, and/or dedifferentiating one or more fat cells. Such effects may be mediated through prostaglandin or prostaglandin-like receptors, and compounds according to the invention may be agonists of such receptors. Cyclopentane heptanoic acid, 2-arylalkyl or cycloalkyl compounds and derivatives thereof, such as bimatoprost, are considered to be members of the class of prostaglandin F2-alpha receptor agonists, which are known to be inhibitors of adipocyte differentiation and survival (Serrero et al. (1992) BIOCHEM. BIOPHYS. RES. COMMUN. 183:438-442; Lepak et al. (1993) PROSTAGLANDINS 46:511-517; Serrero et al. (1995) BIOCHEM. BIOPHYS. RES. COMMUN. 212:1125-1132; Lepak et al. (1995) ENDOCRINOLOGY 136:3222-3229). Accordingly, the fat-reducing properties of these compounds, for example, bimatoprost, may relate to its agonism of prostaglandin or prostaglandin-like receptors. It is contemplated that some of these compounds or derivatives, for example, bimatoprost, may possess physical or pharmacologic properties that render them more suitable for reducing body fat. The present invention is intended to encompass all of the compounds and derivatives described in U.S. Pat. Nos. 5,688,819 and 6,403,649, as well as any and all analogs that can be readily synthesized by one skilled in the art.

The present invention therefore envisions new uses of one or more cyclopentane heptanoic acid, 2-arylalkyl or cycloalkyl compounds or derivatives thereof, such as bimatoprost, as local, topical, transdermal, or intralesional therapy to reduce (or in the extreme, eliminate) deposits of body fat. As such, one or more of these compounds is particularly suitable as a topical, local, or transdermal therapy for any of a number of medical or cosmetic conditions that involve: (1) local excess(es) of body fat; (2) diffuse excess(es) or body fat; (3) maldistribution of body fat; and/or (4) obesity. The invention includes methods of using one or more of these compounds to reduce body fat. The present invention also includes methods of administering one or more of these compounds locally, topically, transdermally, or intralesionally for this purpose. Furthermore, the invention envisions administration of one of more of these compounds to reduce body fat while minimizing or eliminating any significant systemic or local side effects. Numerous pharmaceutical preparations are described that are suitable for application or injection to the skin, mucosa, fat deposits, muscle, or subcutaneous, intramuscular, subdermal, intradermal, subconjunctival, peribulbar, or retrobulbar tissues or spaces. The invention further includes methods for using one or more of these compounds in combination with other methods to reduce body fat.

A. Compounds and Derivatives Relating to the Present Invention

The present invention relates to the use of certain cyclopentane heptanoic acid, 2-cycloalkyl or arylalkyl compounds and derivatives thereof as therapeutic agents, for example, to reduce (or in the extreme, eliminate) body fat (alternatively known as adipose tissue). These therapeutic agents are represented by compounds having the structural formula I

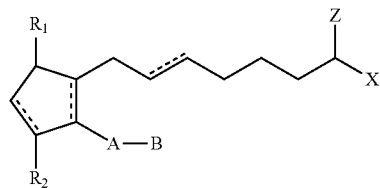

as defined above. Certain nonacidic cyclopentane heptanoic acid, 2-(phenyl alkyl or phenyloxyalkyl) compounds used in accordance with the present invention are encompassed by structural formula VI

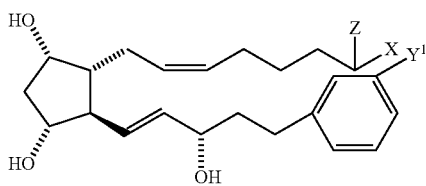

and their 9- and/or 11- and/or 15-esters. Furthermore, an embodiment of the present invention utilizes bimatoprost, also referred to as cyclopentane N-ethyl heptenamide-5-cis-2-(3α-hydroxy-5-phenyl-1-trans-pentenyl)-3,5-dihydroxy, [$1_\alpha$, $2_\beta$, $3_\alpha$, $5_\alpha$] (see U.S. Pat. No. 6,403,649), or (Z)-7-[(1R,2R,3R,5S)-3,5-Dihydroxy-2-[1E,3S)-3-hydroxy-5-phenyl-1-pentenyl]cyclopentyl]-5-N-ethylheptenamide, the compound represented by formula IV

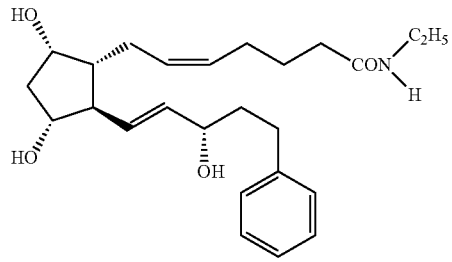

for which the substituents and symbols are as hereinabove defined. Certain compounds utilized in the present invention are represented by formula II

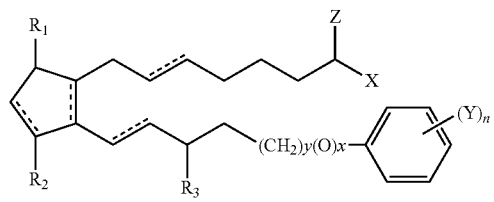

for which the substituents and symbols are as defined above. Additional compounds utilized in the present invention are represented by formula III

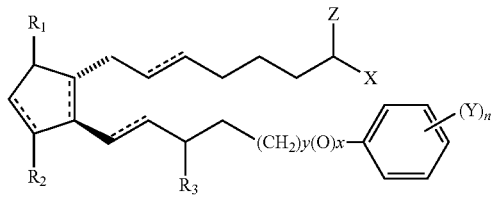

for which the substituents and the symbols are as defined above. Further alternative compounds utilized in the present invention are represented by formula V

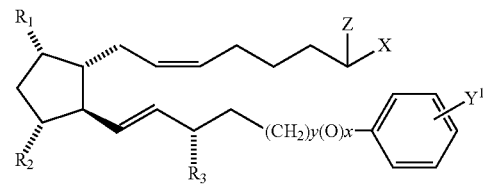

In all of the above formulae, as well as in those provided hereinafter, dotted lines on bonds between carbons 5 and 6 (C-5), between carbons 13 and 14 (C-13), between carbons 8 and 12 (C-8), and between carbons 10 and 11 (C-10) indicate a single or a double bond which can be in the cis or trans configuration. Two solid lines indicate a double bond. Hatched lines at positions C-9, C-11 and C-15 indicate the α configuration. If one were to draw the β configuration, a solid triangular line would be used.

In the compounds used in accordance with the present invention, compounds having the C-9 or C-11 or C-15 substituents in the α or β configuration are contemplated. As hereinabove mentioned, in all formulae provided herein broken line attachments to the cyclopentane ring indicate substituents in the α configuration. Thickened solid line attachments to the cyclopentane ring indicate substituents in the β configuration. Also, the broken line attachment of the hydroxyl group or other substituent to the C-11 and C-15 carbon atoms signifies the α configuration.

For the purpose of this invention, unless further limited, the term "alkyl" refers to alkyl groups having from one to ten carbon atoms. The term "cycloalkyl" refers to cycloalkyl groups having from three to seven carbon atoms. The term "aryl" refers to both substituted and unsubstituted aryl groups having from four to ten carbon atoms. The term "saturated or unsaturated acyclic hydrocarbon group" is used to refer to straight or branched chain, saturated or unsaturated hydrocarbon groups having from one to about 6, alternatively one to about 4, carbon atoms. Such groups include alkyl, alkenyl and alkynyl groups of appropriate lengths. In certain embodiments, such groups include an alkyl, for example, methyl, ethyl, propyl, butyl, pentyl, or hexyl, or an isomeric form thereof.

The definition of $R_6$ may include a cyclic component, $—(CH_2)_m R_7$, in which m is 0 or an integer of from 1 to 10, $R_7$ is an aliphatic ring from about 3 to about 7 carbon atoms, or an aromatic or heteroaromatic ring. The "aliphatic ring" may be saturated or unsaturated, for example, a saturated ring having 3-7 carbon atoms, inclusive. As an aromatic ring, $R_7$ can be phenyl, and the heteroaromatic rings can have oxygen, nitrogen or sulfur as a heteroatom, i.e. $R_7$ may be thienyl, furanyl, pyridyl, etc. In certain embodiments, m is 0 or an integer of from 1 to 4.

Z is =O or represents two hydrogen atoms.

X may be selected from the group consisting of $—OR^4$ and $—N(R^4)_2$ in which $R^4$ is selected from the group consisting of hydrogen, a lower alkyl radical having from one to six carbon atoms, and

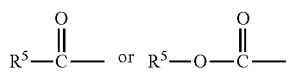

in which $R^5$ is a lower alkyl radical having from one to six carbon atoms.

A compound within the scope of the present invention is bimatoprost, shown as structural formula IV

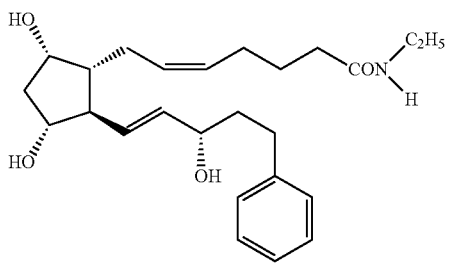

and pharmaceutically acceptable salts thereof. Bimatoprost is an example of a prostamide, and prostamides can be useful according to the present invention. The present invention also relates to modified forms of bimatoprost, for example, bimatoprost with its amide group removed.

Another compound within the scope of the present invention is latanoprost, shown as structural formula VII

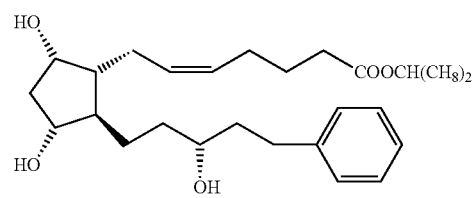

and pharmaceutically acceptable salts thereof. Latanoprost is an example of a compound expected to have utility and effects on fat similar to that described for bimatoprost and other compounds disclosed herein.

Another compound within the scope of the present invention is travoprost, shown as structural formula VIII

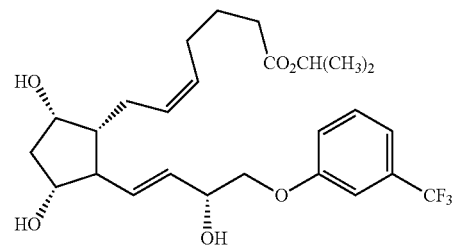

and pharmaceutically acceptable salts thereof. Travoprost is an example of a compound expected to have utility and effects on fat similar to that described for bimatoprost and other compounds disclosed herein.

Alternative compounds within the scope of the present invention are the compounds of formula V

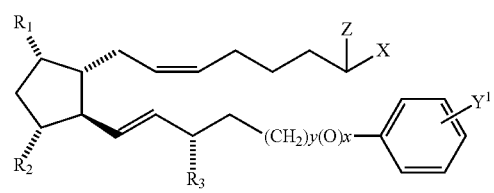

in which X is —OH, i.e. cyclopentane heptanoic acid, 5-cis-2-(3α-hydroxy-4-m-chlorophenoxy-1-trans-butenyl)-3,5-dihydroxy, [$1_α$, $2_β$, $3_α$, $5_α$] and cyclopentane methylheptenoate-5-cis-2(3α-hydroxy-4-m-chlorophenoxy-1-trans-butenyl)-3, 5 dihydroxy, [$1_α$, $2_β$, $3_α$, $5_α$] and the 9- and/or 11- and/or 15-esters of this compound. (The numbered designations in brackets refer to the positions on the cyclopentane ring.)

In addition, the following compounds may be used in the pharmaceutical compositions and the methods of treatment of the present invention: cyclopentane heptenol-5-cis-2-(3α-hydroxy-5-phenyl-1-trans-pentenyl)-3,5-dihydroxy, [$1_α$, $2_β$, $3_α$, $5_α$]; cyclopentane heptenamide-5-cis-2-(3α-hydroxy-5-phenyl-1-trans-pentenyl)-3,5-dihydroxy, [$1_α$, $2_β$, $3_α$, $5_α$]; cyclopentane N,N-dimethylheptenamide-5-cis-2-(3α-hydroxy-5-phenyl-1-trans-pentenyl)-3,5-dihydroxy, [$1_α$, $2_β$, $3_α$, $5_α$]; cyclopentane heptenyl methoxide-5-cis-2-(3α-hydroxy-5-phenyl-1-trans-pentenyl)-3, 5-dihydroxy, [$1_α$, $2_β$, $3_α$, $5_α$]; cyclopentane heptenyl ethoxide-5-cis-2-(3α-hydroxy-4-meta-chlorophenoxy-1-trans-pentenyl)-3,5-dihydroxy, [$1_α$, $2_β$, $3_α$, $5_α$]; cyclopentane heptenylamide-5-cis-2-(3α-hydroxy-4-meta-chlorophenoxy-1-trans-pentenyl)-3, 5-dihydroxy, [$1_\alpha$, $2_\beta$, $3_\alpha$, $5_\alpha$]; cyclopentane heptenylamide-5-cis-2-(3α-hydroxy-4-trifluoromethylphenoxy-1-trans-pentenyl)-3, 5-dihydroxy, [$1_\alpha$, $2_\beta$, $3_\alpha$, $5_\alpha$]; cyclopentane N-isopropyl heptenamide-5-cis-2-(3α-hydroxy-5-phenyl-1-trans-pentenyl)-3,5-dihydroxy, [$1_\alpha$, $2_\beta$, $3_\alpha$, $5_\alpha$]; cyclopentane N-methyl heptenamide-5-cis-2-(3α-hydroxy-5-phenyl-1-trans-pentenyl)-3,5-dihydroxy, [$1_\alpha$, $2_\beta$, $3_\alpha$, $5_\alpha$]; cyclopentane heptenol-5-cis-2-(3α-hydroxy-4-meta-chlorophenoxy-1-trans-butenyl)-3,5-dihydroxy, [$1_\alpha$, $2_\beta$, $3_\alpha$, $5_\alpha$]; cyclopentane heptenamide-5-cis-2-(3α-hydroxy-4-meta-chlorophenoxy-1-trans-butenyl)-3,5-dihydroxy, [$1_\alpha$, $2_\beta$, $3_\alpha$, $5_\alpha$]; and cyclopentane heptenol-5-cis-2-(3α-hydroxy-5-phenyl-1-trans-pentenyl)3,5-dihydroxy, [$1_\alpha$, $2_\beta$, $3_\alpha$, $5_\alpha$].

B. Pharmaceutical Formulations

In certain embodiments, one or more cyclopentane heptanoic acid, 2-cycloalkyl or arylalkyl compounds or derivatives thereof are incorporated into a pharmaceutical formulation containing a pharmaceutically acceptable carrier that is generally suited to local, topical, transdermal, or intralesional drug administration and including any such material known in the art.

"Therapeutically effective amount" means the level, amount or concentration of an agent (i.e., an active pharmaceutical ingredient, such as bimatoprost) needed to treat a disease, disorder or condition without causing significant negative or adverse side effects to the treated tissue.

"Pharmaceutically acceptable salt" is any salt which retains the activity of the parent compound and does not impart any deleterious or undesirable effect on the subject to whom it is administered and in the context in which it is administered. Such salts are those formed with pharmaceutically acceptable cations, e.g., alkali metals, alkali earth metals, etc.

"Local administration" or "locally administering" means administration (i.e. by injection, implantation, or topical application) by a non-systemic route (such as by a topical, subcutaneous, intramuscular, subdermal, intradermal, transdermal, intralesional, or ophthalmic route, whereby insignificant amounts of the pharmaceutical agent appear systemically) of a pharmaceutical agent to or to the vicinity of a target dermal, subdermal, or intralesional area (such as subcutaneous fat) of a patient. For the purpose of the present invention, "injection" means administration by subcutaneous, intramuscular, subdermal, intradermal, intralesional, subconjunctival, peribulbar, or retrobulbar routes.

Pharmaceutical compositions may be prepared by combining a therapeutically effective amount of at least one compound according to the present invention, or a pharmaceutically acceptable salt thereof, as an active ingredient, with conventional topically or locally acceptable pharmaceutical excipients, and by preparation of unit dosage forms suitable for topical or local use. These formulations are described below. The therapeutically effective amount typically is between about 0.0001 and about 5% (w/v), for example, about 0.001 to about 1.0% (w/v) in liquid formulations. The actual dose of the active compounds of the present invention depends on the specific compound, and on the condition to be treated.

Suitable carriers for the compounds according to the invention are available, and the selection of the carrier will depend upon the form of the intended pharmaceutical formulation, e.g., as a solution, ointment, lotion, cream, foam, microemulsion, gel, oil, spray, salve, or the like, and may include naturally occurring and/or synthetic materials. It is understood that the selected carrier should not adversely affect the cyclopentane heptanoic acid, 2-cycloalkyl or arylalkyl compound or derivative thereof, or other components of the pharmaceutical formulation.

Suitable carriers for these types of formulations include, but are not limited to, water, saline, or other aqueous or nonaqueous solutions or suspensions. Other preferred carriers include Shephard's™ Cream, Aquaphor™, and Cetaphil™ lotion. Other preferred carriers include ointment bases, e.g., polyethylene glycol-1000 (PEG-1000), conventional creams such as HEB cream, gels, as well as petroleum jelly and the like. Examples of suitable carriers for use herein include water, alcohols and other nontoxic organic solvents, glycerin, mineral oil, silicone, petroleum jelly, lanolin, fatty acids, vegetable oils, parabens, waxes, and the like. Particularly preferred formulations herein are colorless, odorless solutions, ointments, lotions, creams, microemulsions and gels.

Ointments are semisolid preparations that are typically based on petrolatum or other petroleum derivatives. The specific ointment base to be used, as will be appreciated by those skilled in the art, is one that will provide for optimum drug delivery, and will provide for other desired characteristics as well, e.g., emolliency or the like. As with other carriers or vehicles, an ointment base should be inert, stable, nonirritating and nonsensitizing. As explained in Remington's Pharmaceutical Sciences, 20th ed. (Easton, Pa.: Mack Publishing Company, 2000), ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols (PEGs) of varying molecular weight; again, reference may be had to Remington's, supra, for further information.

Lotions are preparations to be applied to the skin surface of an individual, for example a mammal, for example, a human, without friction, and are typically liquid or semiliquid preparations in which solid particles, including the active agent, are present in a water or alcohol base. Lotions are usually suspensions of solids and can include a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. Certain formulations for use in conjunction with the present invention contain propylene glycol mixed with a hydrophilic petrolatum such as that which may be obtained under the trademark Aquaphor™ from Beiersdorf, Inc. (Norwalk, Conn.).

Creams containing the active agent can be viscous liquid or semisolid emulsions, either oil-in-water or water-in-oil. Cream bases are water-washable, and contain an oil phase, an emulsifier, and an aqueous phase. The oil phase is generally includes petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic, or amphoteric surfactant.

Microemulsions are thermodynamically stable, isotropically clear dispersions of two immiscible liquids, such as oil and water, stabilized by an interfacial film of surfactant molecules (Encyclopedia of Pharmaceutical Technology, vol. 9 (1992) New York: Marcel Dekker). For the preparation of microemulsions, a surfactant (emulsifier), a co-surfactant (co-emulsifier), an oil phase, and a water phase are necessary. Suitable surfactants include any surfactants that are useful in the preparation of emulsions, e.g., emulsifiers that are typically used in the preparation of creams. The co-surfactant (or "co-emulsifer") is generally selected from the group of polyglycerol derivatives, glycerol derivatives, and fatty alcohols. Certain emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, for example, lower molecular weight polyethylene glycols (e.g., PEG 300 and PEG 400), and/or glycerol, and the like, while the oil phase will generally include, for example, fatty acid esters, modified vegetable oils, silicone oils, mixtures of mono-di- and triglycerides, mono- and di-esters of PEG (e.g., oleoyl macrogol glycerides), and so forth.

Gel formulations are semisolid systems including of either small inorganic particle suspensions (two-phase systems) or large organic molecules distributed substantially uniformly throughout a carrier liquid (single phase gels). Single phase gels can be made, for example, by combining the active agent, a carrier liquid and a suitable gelling agent such as tragacanth (at 2 to 5%), sodium alginate (at 2-10%), gelatin (at 2-15%), methylcellulose (at 3-5%), sodium carboxymethylcellulose (at 2-5%), carbomer (at 0.3-5%) or polyvinyl alcohol (at 10-20%) together and mixing until a characteristic semisolid product is produced. Other suitable gelling agents include methylhydroxycellulose, polyoxyethylene-polyoxypropylene, hydroxyethylcellulose and gelatin. Although gels commonly employ aqueous carrier liquid, alcohols and oils can be used as the carrier liquid as well.

A variety of sustained-release formulations, such as patches, pills, or implantable depots, can used in connection with the present invention and readily made by one skilled in the art.

Various additives may be included in the topical formulations of the invention. Examples of additives include, but are not limited to, solubilizers, skin permeation enhancers, opacifiers, preservatives (e.g., anti-oxidants), gelling agents, buffering agents, surfactants (particularly nonionic and amphoteric surfactants), emulsifiers, emollients, thickening agents, stabilizers, humectants, colorants, fragrance, and the like. Inclusion of solubilizers and/or skin permeation enhancers is particularly preferred, along with emulsifiers, emollients, and preservatives.

Examples of solubilizers include, but are not limited to, the following: hydrophilic ethers such as diethylene glycol monoethyl ether (ethoxydiglycol, available commercially as Transcutol™) and diethylene glycol monoethyl ether oleate (available commercially as Softcutol™); polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 400, and polyethylene glycol derivatives such as PEG-8 caprylic/capric glycerides (available commercially as Labrasol™); alkyl methyl sulfoxides such as DMSO; pyrrolidones such as 2-pyrrolidone and N-methyl-2-pyrrolidone; and DMA. Many solubilizers can also act as absorption enhancers. A single solubilizer may be incorporated into the formulation, or a mixture of solubilizers may be incorporated therein.

Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

Other active agents may also be included in the formulation, e.g., anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

Also, the pharmaceutical formulation may be sterilized or mixed with auxiliary agents, e.g., preservatives, stabilizers, wetting agents, buffers, or salts for influencing osmotic pressure and the like. Sterile injectable solutions can be prepared by incorporating one or more cyclopentane heptanoic acid, 2-cycloalkyl or arylalkyl compounds or derivatives thereof in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

For ophthalmic application, solutions typically are prepared using a physiological saline solution as a major vehicle. The pH of such ophthalmic solutions should be maintained between 4.5 and 8.0 with an appropriate buffer system, a neutral pH being preferred but not essential. The formulations may also contain conventional, pharmaceutically acceptable preservatives, stabilizers and surfactants.

Certain preservatives that may be used for ophthalmic preparation(s) include, but are not limited to, benzalkonium chloride, chlorobutanol, thimerosal, phenylmercuric acetate and phenylmercuric nitrate. One surfactant that may be used is, for example, Tween 80. Likewise, various vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water. Tonicity adjustors may be added as needed or convenient. They include, but are not limited to, salts, particularly sodium chloride, potassium chloride, mannitol and glycerin, or any other suitable ophthalmically acceptable tonicity adjustor. Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed. In a similar vein, an ophthalmically acceptable antioxidant for use in ophthalmic preparation(s) includes, but is not limited to, sodium metabisulfite, sodium thiosulfate, acetylcysteine, butylated hydroxyanisole and butylated hydroxytoluene.

C. Uses of the Compositions and Compounds of the Invention

The present invention uses one or more cyclopentane heptanoic acid, 2-arylalkyl or cycloalkyl compounds and derivatives thereof to reduce (or in the extreme, eliminate) body fat. For the purpose of this invention, unless further limited, the term "reduce" means to diminish the volume, size, mass, bulk, density, amount, and/or quantity of a substance. The present invention is expected to reduce fat by greater than or equal to 50%, by greater than or equal to 25%, by greater than or equal to 10%, and/or by greater than or equal to 5%. For example, fat reduction can include reducing fat cell amount (for example, fat cell number), reducing fat cell volume, reducing fat cell maturation, and/or dedifferentiating a fat cell.

Specifically, the invention envisions new uses for these compounds when administered locally or topically to the skin, fat deposits, muscle, subcutaneous space, intramuscular space, eye, orbital tissue, orbital space(s), tumor, lesion, or mucous membrane of an individual, for example, a mammal, for example, a human. The invention contemplates special usefulness for individuals with obesity, fat maldistribution, or cosmetic disturbances of excess or maldistributed body fat, whether local or diffuse.

The invention is further expected to be useful for individuals with prominent or undesired deposits of fat on the abdomen, chest, buttocks, hips, thighs, legs, knees, arms, chin, face, or neck. The invention is also conceived to be beneficial for individuals with Cushing syndrome, pseudo-Cushing syndrome, drug-induced obesity, HIV-related lipodystrophy, hypothyroidism, pseudohypoparathyroidism, hypothalamic obesity, polycystic ovarian disease, depression, binge eating, Prader-Willi syndrome, Bardet-Biedl syndrome, Cohen syndrome, Down syndrome, Turner syndrome, growth hormone deficiency, growth hormone resistance, or leptin deficiency or resistance. The invention is further contemplated to be of utility for individuals using cortisol and analogs, other corticosteroids, megace, sulfonylureas, trycyclic antidepressants, monoamine oxidase inhibitors, selective serotonin reuptake inhibitors, oral contraceptives, insulin, risperidone, clozapine, and thiazolidindiones.

It is of note that corticosteroids, which cause inappropriate local accumulations of fat on various body parts (Cushingoid appearance), are potent inhibitors of prostaglandin pathways, and that this antiprostaglandin activity may mediate the Cushingoid appearance. The compounds and derivatives of the present invention may therefore be useful as specific, local opponents to this process in individuals on systemic corticosteroid therapy.

The invention is also conceived to be useful for individuals with any hormonal status, including physiologic changes such as pregnancy or menopause, that results in excess body fat. The invention is further envisioned to be beneficial for treating weight gain or excess body fat in individuals who are undergoing or who have recently undergone smoking cessation. Further uses of the invention include treatment of individuals for whom immobility or disuse of an extremity favors the accumulation of excess body fat. The invention is also contemplated to be useful for individuals with thyroid orbitopathy (Grave's disease), whereby reduction of orbital fat may lead to improvement of exophthalmos, eyelid displacement, signs and symptoms or ocular exposure, or optic neuropathy. It is further envisioned that the invention will be useful for achieving weight loss in individuals who have suffered hip fractures. Likewise, the invention is expected to be useful for astronauts and others who face prolonged periods of immobility.

The invention may also be beneficial in the treatment of fatty tumors such as lipomas, regardless of where they occur in the body.

The invention may also be useful as an adjunct to other cosmetic or surgical procedures, including but not limited to, mammoplasty, blepharoplasty, abdominoplasty, lipoplasty (liposuction), rhinoplasty, botulinum toxin (Botox™) administration, transverse rectus abdominis muscle (TRAM) flap, orbital decompression, midface lift, sub-orbicularis oculi fat (SOOF) lift, and brow lift.

The invention may also be useful as an adjunct to any of various kinds of surgery, whether used in the pre-operative, peri-operative, or post-operative period. The invention further contemplates uses preceding abdominal, thoracic, oncologic, endocrine, neurologic, transplant, and dermatologic surgery, whereby surgical exposure may be improved; and preceding or following orthopedic procedures, whereby surgical exposure as well as post-operative recovery may be improved.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps. Further, it should be understood that the order of steps or order for performing certain actions are immaterial so long as the invention remains operable. Moreover, two or more steps or actions may be conducted simultaneously.

EXAMPLES

In light of the foregoing description, the specific non-limiting examples presented below are for illustrative purposes and not intended to limit the scope of the invention in any way. In Examples 4-8, various modes of non-systemic administration of a cyclopentane heptanoic acid, 2-arylalkyl or cycloalkyl compound or derivative thereof can be used, for example, by topical application (ointment, cream, or transdermal patch), subcutaneous injection, intramuscular injection, or intralesional injection, any of which may involve a controlled (or sustained) release formulation or depot.

Example 1. In Vitro Study of Mouse Preadipocyte Viability, Preadipocyte Differentiation, Preadipocyte Apoptosis, and Adipocyte Apoptosis The following experiment describes administration of bimatoprost, an example of compounds according to the invention, to adipocytes and preadipocytes to determine cell viability, apoptosis, and cell differentiation as a function of the presence of bimatoprost and/or as a function of the concentration of bimatoprost. The protocol is generally adapted from Lin et al. (2005) OBESITY 13: 982-990.

Preparation of Preadipocytes.

3T3-L1 mouse embryo fibroblasts are obtained and cultured. Cells are cultured at 37° C. in a humidified 5% $CO_2$ atmosphere and grown in Dulbecco's modified Eagle's medium (DMEM) with 10% bovine calf serum. Confluency is induced for 2 days (Days −1 and 0) and preadipocytes are cultured in DMEM with 10% fetal bovine serum (FBS/DMEM) medium, supplemented with 167 nM insulin, 0.5 μM isobutylmethylxanthine, and 1 μM dexamethasone for 2 days (Days 1 and 2).

Preparation (Induction) of Mature Adipocytes from Preadipocytes.

Preadipocytes prepared as above are then maintained in a culture medium with 167 nM insulin supplement for another 2 days (Days 3 and 4), followed by culturing with 10% FBS/DMEM medium for an additional 4 days (Days 5-8), at which time >90% of the cells are expected to have differentiated and matured into adipocytes with accumulated fat droplets. All media contains 100 U/mL penicillin, 100 μg/mL streptomycin, and 292 μg of L-glutamine/mL.

All experiments, except where otherwise indicated, are performed with bimatoprost added to the culture medium for a final concentration of 0%, 0.003%, 0.03%, or 0.3% for a duration of 3, 6, 12, or 24 hours [with 1:1000 dimethyl sulfoxide (DMSO)]. In alternative experimental protocols according to this example, the duration of exposure to bimatoprost is on the order of days, weeks, or months. To the extent longer exposure times are desired, certain aspects of the experimental protocols described in this example are altered accordingly, for example, to maintain cell viability in culture over longer periods of exposure.

Test for Cell Viability.

Standard MTS tests of cell viability are performed in 96-well plates. MTS is a tetrazolium compound that is converted to formazan within metabolically active cells. Non-viable cells do not perform this conversion. For mature adipocytes, seeding density is 5000 cells/well, and cells undergo induction until matured. For preadipocytes, seeding density is 2500 cells/well, and cells are cultured overnight before treatment (with an expected doubling time of approximately 18 hours). Cells are incubated with either DMSO (1:1000) or increasing concentrations of bimatoprost for up to 24 hours. The medium is then changed and replaced with 100 μL of fresh 10% FBS and 20 μL of MTS solution (Promega, Madison, Wis.). Cells are then returned to the incubator for an additional 2 hours before 25 μL of 10% sodium dodecyl sulfate is added to stop the reaction. The plate is analyzed by spectrometry at a wavelength of 490 nm, which is an absorbance peak for formazan. The quantity of formazan as measured by absorbance at 490 nm is a directly proportional to the number of viable cells.

Test for Apoptosis (1).

Laser scanning cytometry (LSC) is employed to detect apoptosis-mediated disruption of the plasma membrane. Mature adipocytes are incubated with either DMSO (1:1000) or increasing concentrations of bimatoprost for 24 hours. Monolayer cells from each treatment are washed twice with cold phosphate-buffered saline (PBS) and once in binding buffer and then incubated in the dark with gentle agitation for 10 minutes with 5 μL of annexin V-fluorescein isothiocyanate (AV, which binds phosphatidylserine) and 5 μL of propidium iodide (PI) in 450 μL of binding buffer (BD Biosciences, San Diego, Calif.) at ambient temperature. LSC is carried out as previously described in the art. Apoptotic cells fluoresce and are detected by LSC, since AV binds specifically to phosphatidylserine in the disrupted plasma membrane. PI, which binds specifically to double-stranded DNA, is only exposed to extracellular milieu in late apoptosis or cell death. Cells are therefore characterized as follows: viable (low AV and PI intensity), apoptotic (high AV and low PI intensity), or dead (high PI intensity).

Test for Apoptosis (2).

Terminal Deoxynucleotidyl Transferase dUTP Nick-End Labeling (TUNEL) Imaging is one of the most common assays for apoptosis. The TUNEL method incorporates labeled terminal nucleotides to detect apoptosis-mediated cleavage and degradation of DNA. Both preadipocytes and mature adipocytes are incubated with or without bimatoprost for 24 hours. An APO-BrdU TUNEL kit can obtained from a supplier. Monolayer cells are fixed with 10% formalin (PBS buffered) and stored in 70% ethanol at −20° C. for 24 hours. Cells are washed twice in the washing buffer, followed by one-hour incubation in a humidity box at 37° C. with gentle agitation in 150 μL of DNA-labeling solution (containing 30 μL of reaction buffer, 2.25 μL of terminal deoxynucleotidyl transferase, 24 μL of BrdUTP, and 93.754 of $dH_2O$). After a brief wash, the cells are incubated for 30 minutes with Alexa Fluor 488 dye-labeled anti-BrdU antibody (1:20 dilution), followed by an additional 30 minutes with PI/RNase buffer to stain the nucleus at room temperature in the dark, and viewed with a fluorescent microscope. Apoptosis manifests as fluorescence upon microscopic examination, which reflects the antibody-labeled BrdU incorporated at the cleaved portions of DNA.

Test for Differentiation of Preadipocytes into Mature Adipocytes.

Oil-Red-O, a specific lipid stain, is used to test the effect of bimatoprost on adipogenesis. Three final concentrations of bimatoprost (0.003%, 0.03%, and 0.3% μM), along with 1:1000 DMSO control are added with the induction medium (see schedule above) in addition to no-addition normal controls. The medium is changed every 2 days. To identify cells undergoing adipogenesis, cells are stained with Oil-Red-O. Briefly, dishes are washed with cold PBS and fixed in 10% neutral formalin. After two changes of propylene glycol, Oil-Red-O is added with agitation for 7 minutes, followed by washing in 85% propylene glycol. The dishes are then rinsed in distilled water and counterstained with hematoxylin. For each dish, multiple images are taken and analyzed for average lipid droplet size, percentage lipid area, and total droplet number with software. Lipid droplets appear as red-stained features.

Results.

Specific observations which are anticipated include: (1) on MTS testing, lower absorbance at 490 nm of bimatoprost-treated cells compared to control cells; (2) on laser scanning cytometry (LSC), more AV-labeled and/or PI-labeled (apoptotic or dead) cells among bimatoprost-treated samples compared to control samples; (3) on TUNEL imaging, more BrdU-antibody-labeled (fluorescent) cells among bimatoprost-treated samples compared to control samples; and (4) on Oil-Red-O staining, smaller and fewer lipid droplets seen on bimatoprost-treated samples compared to control samples (reflecting a lower degree of differentiation of preadipocytes into adipocytes).

Conclusion.

The experiments described above are designed to and are contemplated to provide a conclusion that (1) preadipocytes and/or mature adipocytes treated with bimatoprost have lower rates of viability compared to control samples; (2) preadipocytes and/or mature adipocytes treated with bimatoprost have higher rates of apoptosis compared to control samples; and/or (3) preadipocytes treated with bimatoprost have lower rates of differentiation into mature adipocytes compared to control samples. These results may correlate in a dose-dependent manner within a range of bimatoprost administration. As a result, these contemplated outcomes will show, in vitro, that compounds according to the present invention, including bimatoprost, can reduce fat in one or more of a variety of ways, including cell death and reduced cell maturation.

Example 2. In Vivo Rodent Study

The following experiment describes a randomized study in laboratory rodents to test whether compounds according to the invention, including topical bimatoprost, reduce total body fat mass, subcutaneous fat mass, and total body mass.

Animal Preparation.

Genetically uniform laboratory rodents (for example, hairless rats or nude mice) are used. They are adult laboratory rodents similar in size at the commencement of the study (approximately postnatal week 15 for rats). Multiple animals are tested. Animals randomized to bimatoprost are housed separately from control animals but are kept in the same room under identical environmental conditions. All animals are fed a standard diet, appropriate for the species, ad libitum.

Method.

In all cases the vehicle is a compatible ointment, such as petrolatum, with a final bimatoprost concentration of 0%, 0.003%, 0.03%, or 0.3%. A fixed amount of ointment, for example 1 gram, is applied daily in a thin film over a uniform surface area of the abdominal skin of each animal. Each animal is randomized to a daily application of a dose of topical bimatoprost or vehicle alone. On a weekly basis, total body mass of each animal is determined on a scale. Total body fat is estimated by any of the several methods established for this purpose, for example, water displacement (Dahms et al. (1982) J NUTR. 112: 398-400), isotopic dilution (Culebras et al. (1977) J. PHYSIOL. 232: R60-65), Total Body Electrical Conductance (TOBEC) (Baer et al. (1993) PHYSIOL. BEHAV. 53: 1195-99), Dual-Energy X-Ray Absorptiometry (DEXA) (Bertin et al. (1998) J NUTRITION 128: 1550-54), or Nuclear Magnetic Resonance (NMR) (Kunnecke et al. (2004) OBES RES. 12: 1604-15). Animals are maintained and monitored in this fashion for six months, at which point they are sacrificed.

Analysis and Results.

Abdominal fat pads of the sacrificed animals are excised and measured directly for mass and volume. Direct carcass analysis with chemical extraction may be further performed (Frisch et al. (1977) PNAS 74: 379-383). All results are normalized with reference to baseline values and then compared between bimatoprost and control groups.

Conclusion.

It is contemplated that the experiment described above will indicate that animals treated with compounds according to the present invention, in this case bimatoprost, will exhibit lower total body fat mass, lower subcutaneous (abdominal) fat mass, and/or lower total body mass compared to control animals. These results may correlate in a dose-dependent manner within a range of bimatoprost administration. As a result, these contemplated outcomes will show, in vivo, that compounds according to the present invention, including bimatoprost, can reduce fat.

Example 3. In Vivo Human Study

The following experiment describes a randomized, double-blind study in human subjects to test whether compounds according to the invention, including topical bimatoprost, reduces fat in the body of individuals.

Multiple human subjects (both male and female), for example, with body mass indices of 30 or more but otherwise healthy, are entered into a randomized double-blind study. Either the left or the right arm is randomized to receive topical bimatoprost; the other arm receives vehicle only. Bimatoprost is supplied in a petrolatum-based ointment (the vehicle) at a final concentration of 0%, 0.003%, 0.03% or 0.3%. Ointment containers are unlabeled as to the presence or concentration of bimatoprost.

Each day, subjects apply a thin film of ointment to the skin over the respective triceps while wearing new, clean surgical gloves. Subjects are instructed to refrain from washing the treated area for at least 8 hours and are instructed to refrain from wearing tight clothing or occlusive dressings that will come into contact with the treated area.

Body fat calipers are used to measure fat in the triceps region bilaterally on a weekly basis. The study continues for 6 months. It is contemplated that the experiments described above will indicate that body areas, such as arms, treated with compounds according to the present invention, including bimatoprost, will exhibit lower fat compared to control areas, such as arms, treated with vehicle alone. These results may correlate in a dose-dependent manner within a range of bimatoprost administration. As a result, this contemplated outcome will show, in vivo, that compounds according to the present invention, including bimatoprost, can reduce fat.

Example 4: Use of Cyclopentane Heptanoic Acid, 2-Arylalkyl or Cycloalkyl Compounds and Derivatives Thereof to Reduce Obesity The following description exemplifies a clinical application of a cyclopentane heptanoic acid, 2-arylalkyl or cycloalkyl compound or a derivative thereof to treat obesity.

A 52-year-old man is diagnosed with type 2 diabetes and hypertension. Medical evaluation reveals that his height is 5 feet 8 inches and a weight of 211 pounds, corresponding to a body mass index (BMI) of 32.1 (clinically obese). His noninvasive blood pressure is 184/98. His fasting serum glucose is 147 and his hemoglobin A1C is 7.6. His physical exam is notable for prominent central (abdominal) obesity.

In addition to medical therapy, the man's physician recommends a regimen of diet and exercise. After six months the man is unable to lose weight. The physician prescribes daily topical application of a bimatoprost ointment to the abdomen as treatment for central obesity. After a period of time, for example from a few days to several months, the man's BMI is reduced and/or abdominal fat deposits are reduced.

Example 5: Use of Cyclopentane Heptanoic Acid, 2-Arylalkyl or Cycloalkyl Compounds and Derivatives Thereof to Treat Signs and Symptoms of Cushing Disease The following description exemplifies a clinical application of a cyclopentane heptanoic acid, 2-arylalkyl or cycloalkyl compound or a derivative thereof to treat Cushing disease.

A 19-year-old woman with severe persistent asthma is dependent on high-dose prednisone for several months. Although she is able to maintain normal weight (BMI 21), there are pronounced fatty deposits on her cheeks (so-called "moon facies") and a fat pad between her shoulders (so-called "buffalo hump"). She is diagnosed with Cushing syndrome secondary to prolonged prednisone therapy. Attempts to taper the prednisone are thwarted by multiple asthma exacerbations requiring hospitalization, including one requiring intubation.

The woman's physician prescribes a daily application of a bimatoprost ointment to the face and between the shoulders as treatment for the fat deposits. After a period of time, for example from a few days to several months, the fatty deposits on the woman's cheeks are reduced and/or the fat pad between her shoulders is reduced.

Example 6: Use of Cyclopentane Heptanoic Acid, 2-Arylalkyl or Cycloalkyl Compounds and Derivatives Thereof to Treat Fat Maldistribution Associated with HIV/AIDS The following description exemplifies a clinical application of a cyclopentane heptanoic acid, 2-arylalkyl or cycloalkyl compound or a derivative thereof to treat fat maldistribution associated with HIV/AIDS.

A 34-year-old man with HIV/AIDS uses multiple reverse transcriptase inhibitors and protease inhibitors for seven years, since first being diagnosed as HIV seropositive. Despite normal body weight (BMI 20), there are pronounced fatty deposits on his cheeks (so-called "moon facies") and a fat pad between his shoulders (so-called "buffalo hump"). He is diagnosed with HIV-related fat maldistribution syndrome (lipodystrophy).

The man's physician prescribes a daily application of a bimatoprost ointment to the face and between the shoulders as treatment for the fat deposits. After a period of time, for example from a few days to several months, the fatty deposits on the man's cheeks are reduced and/or the fat pad between his shoulders is reduced.

Example 7: Use of Cyclopentane Heptanoic Acid, 2-Arylalkyl or Cycloalkyl Compounds and Derivatives Thereof to Reduce Local Fat Deposits of Functional and/or Cosmetic Significance The following description exemplifies a clinical application of a cyclopentane heptanoic acid, 2-arylalkyl or cycloalkyl compound or a derivative thereof to reduce local fat deposits of functional and/or cosmetic significance.

A 56-year-old female flight attendant is troubled by prominent fat deposits on her hips and thighs, which interfere with her work and lower her self-esteem. Her physician recommends diet and exercise. The woman loses 7 pounds, but there is no noticeable reduction in the fat deposits. She is referred to a plastic surgeon but declines lipoplasty due to potential adverse effects.

The plastic surgeon prescribes a daily application of a bimatoprost ointment to the hips and thighs as treatment for the fat deposits. After a period of time, for example from a few days to several months, the fatty deposits on the woman's hips and/or thighs are reduced.

Example 8: Use of Cyclopentane Heptanoic Acid, 2-Arylalkyl or Cycloalkyl Compounds and Derivatives Thereof to Treat the Orbitopathy of Grave's Disease (Thyroid Orbitopathy)

The following description exemplifies a clinical application of a cyclopentane heptanoic acid, 2-arylalkyl or cycloalkyl compound or a derivative thereof to treat the orbitopathy of Grave's disease (thyroid orbitopathy).

A 42-year-old woman with Grave's disease sees an oculoplastic specialist for complaints of bilateral eye discomfort. Eye exam reveals normal vision and no evidence of compressive optic neuropathy; however, there is mild bilateral proptosis, lid retraction, and evidence of corneal exposure. The woman wishes to avoid systemic steroids if possible.

The doctor prescribes an ophthalmic preparation of bimatoprost daily to both eyes as a treatment for the proptosis and exposure symptoms. After a period of time, for example from a few days to several months, the woman's orbital fat is reduced and her condition improves.

INCORPORATION BY REFERENCE

The entire disclosure of each of the publications and patent documents referred to herein is incorporated by reference in its entirety for all purposes to the same extent as if each individual publication or patent document were so individually denoted.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for reducing orbital fat, the method comprising administering to an individual suffering from undesired orbital fat a therapeutically effective amount of latanoprost, or a pharmaceutically acceptable salt thereof.

2. The method of claim 1, wherein the latanoprost, or a pharmaceutically acceptable salt thereof, is administered to the skin of the individual's face.

3. The method of claim 2, wherein the step of administering is by topical administration.

4. The method of claim 2, wherein the step of administering is by transdermal administration.

5. The method of claim 2, wherein the step of administering is by injection.

6. The method of claim 2, wherein the step of administering is by implanting an implantable depot of latanoprost, or a pharmaceutically acceptable salt thereof, into the skin.

7. The method of claim 1, wherein the method comprises administering a pharmaceutical composition containing latanoprost, or a pharmaceutically acceptable salt thereof, at a concentration ranging from about 0.001% to about 1.0% (w/v), inclusive.

8. The method of claim 1, wherein the method is performed as an adjunct to a cosmetic or surgical procedure.

9. The method of claim 8, wherein the cosmetic or surgical procedure is selected from the group consisting of rhinoplasty, botulinum toxin, orbital decompression, midface lift, sub-orbicularis oculi fat lift, and brow lift.

10. The method of claim 8, wherein the method is performed as an adjunct to a cosmetic or surgical procedure during the pre-operative period.

11. The method of claim 8, wherein the method is performed as an adjunct to a cosmetic or surgical procedure during the peri-operative period.

12. The method of claim 8, wherein the method is performed as an adjunct to a cosmetic or surgical procedure during the post-operative period.

13. The method of claim 1, wherein the individual suffers from thyroid orbitopathy.

14. The method of claim 1, wherein the individual suffers from prominent facial fat pads.

15. The method of claim 1, wherein the individual suffers from orbital fat prolapse.

16. The method of claim 1, wherein the reduction in the undesired orbital fat leads to an improvement of exophthalmos, eyelid displacement, ocular exposure, or optic neuropathy.

17. The method of claim 1, wherein the undesired orbital fat is a lipoma.

18. The method of claim 1, wherein latanoprost, or a pharmaceutically acceptable salt thereof, is administered to eye, orbital tissue, or orbital spaces.

* * * * *